(12) United States Patent
Kajisa et al.

(10) Patent No.: US 10,996,194 B2
(45) Date of Patent: May 4, 2021

(54) HIGH-SENSITIVITY BIOSENSOR AND METHOD FOR PRODUCING THE SAME

(71) Applicants: PROVIGATE INC., Tokyo (JP); THE UNIVERSITY OF TOKYO, Tokyo (JP)

(72) Inventors: Taira Kajisa, Tokyo (JP); Koshin Sekimizu, Tokyo (JP); Toshiya Sakata, Tokyo (JP)

(73) Assignees: PROVIGATE INC., Tokyo (JP); THE UNIVERSITE OF TOKYO, Tokyo (JP)

( * ) Notice: Subject to any disclaimer, the term of this patent is extended or adjusted under 35 U.S.C. 154(b) by 171 days.

(21) Appl. No.: 16/087,251

(22) PCT Filed: Feb. 21, 2017

(86) PCT No.: PCT/JP2017/006306
§ 371 (c)(1),
(2) Date: Sep. 21, 2018

(87) PCT Pub. No.: WO2017/163715
PCT Pub. Date: Sep. 28, 2017

(65) Prior Publication Data
US 2019/0049405 A1    Feb. 14, 2019

(30) Foreign Application Priority Data

Mar. 25, 2016   (JP) ............... JP2016-061362

(51) Int. Cl.
*G01N 27/327* (2006.01)
*G01N 27/414* (2006.01)
(Continued)

(52) U.S. Cl.
CPC ......... *G01N 27/414* (2013.01); *G01N 27/126* (2013.01); *G01N 27/3272* (2013.01);
(Continued)

(58) Field of Classification Search
CPC ............ G01N 27/414; G01N 27/4145; G01N 27/327; G01N 27/3272
See application file for complete search history.

(56) References Cited

U.S. PATENT DOCUMENTS

2012/0270964 A1   10/2012   Piletsky et al.
2012/0293160 A1   11/2012   Koto et al.
(Continued)

FOREIGN PATENT DOCUMENTS

DE        4338732       5/1995
EP        3159686       4/2017
(Continued)

OTHER PUBLICATIONS

EPO computer-generated English language translation of the Description section of Thomas Dandekar DE 4338732 A1, patent published May 18, 1995, translation downloaded Jul. 26, 2020 (Year: 1995).*
(Continued)

*Primary Examiner* — Alexander S Noguerola
(74) *Attorney, Agent, or Firm* — Myers Bigel, P.A.

(57) ABSTRACT

[Problem to be Solved]
A biosensor having high detection sensitivity and detection specificity is provided.
[Solution]
There is provided a biosensor comprising: an identification substance capable of binding to a substance to be detected; and an electrode charged with a charge of the identification substance, and detecting a change in a charge density of the electrode caused by binding of the substance to be detected to the identification substance, wherein a polymer layer in which a molecular template having a structure complementary to a molecular structure of the substance to be detected is formed is formed on all or part of a surface of the
(Continued)

100: GLUCOSE SENSOR
101: FET DEVICE
102: GATE INSULATING FILM
103: METAL ELECTRODE
104: WIRING
105: SUBSTRATE
106: METAL GATE ELECTRODE
107: MOLECULAR IMPRINTED POLYMER LAYER
108: REFERENCE ELECTRODE
109: GLASS RING
110: BUFFER electrode, the identification substance is contained in the polymer layer, and the polymer layer is an ultrathin film layer.

11 Claims, 9 Drawing Sheets

(51) Int. Cl.
  G01N 27/416 (2006.01)
  G01N 33/02 (2006.01)
  G01N 33/543 (2006.01)
  G01N 33/66 (2006.01)
  G01N 27/12 (2006.01)
(52) U.S. Cl.
  CPC ..... *G01N 27/3273* (2013.01); *G01N 27/3275* (2013.01); *G01N 27/3278* (2013.01); *G01N 27/416* (2013.01); *G01N 27/4145* (2013.01); *G01N 33/02* (2013.01); *G01N 33/5438* (2013.01); *G01N 33/66* (2013.01); *G01N 2610/00* (2013.01)

(56) References Cited

U.S. PATENT DOCUMENTS

| | | | |
|---|---|---|---|
| 2016/0069834 A1 | 3/2016 | Sakata | |
| 2016/0169835 A1 | 6/2016 | Sakata et al. | |
| 2017/0122899 A1* | 5/2017 | Sakata | G01N 27/4145 |

FOREIGN PATENT DOCUMENTS

| | | |
|---|---|---|
| JP | 63021545 | 1/1988 |
| JP | 2007313400 | 12/2007 |
| JP | 2012242172 | 12/2012 |
| JP | 2012246163 | 12/2012 |
| JP | 2013512324 | 4/2013 |
| JP | 201638384 | 3/2016 |
| WO | 2012/124800 | 9/2012 |
| WO | 2014/178237 | 11/2014 |
| WO | 2015/198668 | 12/2015 |

OTHER PUBLICATIONS

Pogorelova et al., "Development of ion-sensitive field-effect transistor-based sensors for benzylphosphonic acids and thiophenols using molecularly imprinted TiO2 films," Analytics Chimica Acta 504 (2004) 113-122 (Year: 2004).*
Erdőssy et al., "Electrosynthesized molecularly imprinted polymers for protein recognition," Trends in Analytical Chemistry 79 (May 2016) 179-190 (Year: 2016).*
Özcan et al., "Electrochemical Preparation of a Molecularly Imprinted Polypyrrole-modified Pencil Graphite Electrode for Determination of Ascorbic Acid," Sensors 2008, 8, 5792-5805 (Year: 2008).*
Iskierko et al. "Extended-gate field-effect transistor (EG-FET) with molecularly imprinted polymer (MIP) film for selective inosine determination," Biosensors and Bioelectronics vol. 74, Dec. 15, 2015, pp. 526-533, plus Supplemental Information, 8 pages (Year: 2015).*
Algieri et al. "Bio-Mimetic Sensors Based on Molecularly Imprinted Membranes", Sensors 14:13863-13912 (2014).
Extended European Search Report corresponding to European Application No. 17769761.2 dated Sep. 30, 2019.
Iskierko et al. "Extended-gate-field-effect transistor (EG-FET) with molecularly imprinted polymer (MIP) film for selective inosine determination", Biosensors and Bioelectronics 74:526-533 (2015).
Peeters et al. "Molecularly Imprinted Polymers (Mips) for Bioanalytical Sensors: Strategies for Incorporation of Mips into Sensing Platforms", Austin J Biosens & Bioelectron 1(3):1011 (2015) (5 pages).
Zaytas et al. "Imprinting of specific molecular recognition sites in inorganic and organic thin layer membranes associated with ion-sensitive field-effect transistors", Tetrahedron 58:815-824 (2002).
International Search Report corresponding to International Application No. PCT/JP2017/006306 dated May 23, 2017.
Written Opinion of the International Searching Authority corresponding to International Application No. PCT/JP2017/006306 dated May 23, 2017.
Notification Concerning Transmittal of International Preliminary Report on Patentability corresponding to International Application No. PCT/JP2017/006306 dated Oct. 4, 2018.
Communication Pursuant to Article 94(3) corresponding to European Application No. 17769761.2 dated Feb. 18, 2021.
Sallacan, Nesim, et al., "Imprinting of Nucleotide and Monosaccharide Recognition Sites in Acrylamidephenylboronic Acid—Acrylamide Copolymer Membranes Associated with Electronic Transducers", Analytica Chemistry, vol. 74, Feb. 2002, 702-712.
Yoshimi, Yasuo, et al., "Development of an enzyme-free glucose sensor using the gate effect of a molecularly imprinted polymer", Journal of Artificial Organs, vol. 12, Dec. 2009, 264-270.

* cited by examiner

HIGH-SENSITIVITY BIOSENSOR AND METHOD FOR PRODUCING THE SAME

RELATED APPLICATION

This application is a 35 U.S.C. § 371 national stage application of International Application No. PCT/JP2017/006306, filed Feb. 21, 2017, which claims the benefit, under 35 U.S.C. § 119 (a) of Japanese Patent Application No. 2016-061362, filed Mar. 25, 2016. The entire content of each is incorporated herein by reference in its entirety.

TECHNICAL FIELD

The present invention relates to a biosensor for detecting a substance to be detected in a test sample.

BACKGROUND ART

In recent years, various biosensors have been researched and developed, and used in the fields of medical treatment, drug development, clinical examination, and the like. Biosensors recognize outside information (for example, a chemical factor) as some physical signal utilizing the excellent molecular identification power that an organism has, and various principles and objects to be measured are used. More specifically, a biosensor is a type of chemical sensor using a chemical substance as an object to be measured, and is composed of a molecular identification element that recognizes only a substance to be measured, and a signal conversion element that converts information that the substance to be measured is recognized into a physical signal such as an electrical signal. Generally, for molecular identification elements, biomolecules such as enzymes, antibodies, DNA, cells, and microorganisms, and compounds that capture biomolecules are used, and therefore these sensors are referred to as biosensors.

As signal conversion elements, usual electronic equipment and chemical sensors such as electrodes, thermistors, crystal oscillators, surface plasmon resonance, and semiconductor elements are used, but recently, research on biosensors using Field Effect Transistors (FETs) has become active. In a biosensor using a FET, when the molecular identification element recognizes a chemical substance that is an object to be measured, a physical change in heat, mass, charge, or the like, or a chemical change such as the decomposition of the target substance or the production of a substance occurs, and this change is converted into an electrical signal by the FET that is a signal conversion element to measure the target substance. The features of a biosensor using a FET are that (1) a charge inherent in an ion or a molecule can be electrically detected, (2) no effort or time before measurement is required, (3) real time measurement is possible, (4) electrical measurement in an unlabeled and noninvasive manner is possible, (5) miniaturization and integration are possible by a semiconductor micromachining technique, and so on.

So far, high sensitivity biosensors have been proposed in which a slight amount of a body fluid sample noninvasively taken can be used, and even when a slight amount of a sample is used, or the concentration of a substance to be measured in a sample is low, the target substance can be measured with high precision (for example, Patent Literature 1).

CITATION LIST

Patent Literature

[Patent Literature 1] WO2014/178237

SUMMARY OF INVENTION

Technical Problem

The biosensor described in the above Patent Literature 1 has been a revolutionary invention in that a slight amount of a substance to be measured that is contained in a body fluid can be measured. But, various substances other than a substance to be measured are contained in a body fluid, and therefore in putting such a biosensor to practical use, it has been necessary not only to enhance detection sensitivity to a substance to be measured, but to prevent false detection of substances other than the substance to be measured (that is, enhance detection specificity).

Solution to Problem

The present inventors have found that by laminating a layer of a (MIP) on the gate electrode of a biosensor, substantially all substances other than a substance to be detected can be prevented from interacting with the gate electrode. As used herein, the molecular imprinted polymer refers to the polymer on the surface of which and in which a "molecular template" having a structure complementary to the molecular structure of a substance to be detected is formed by a predetermined making method, and only the substance to be detected can be incorporated into the molecular template.

Further, the present inventors have further repeated research for the practical use of a biosensor in which a molecular imprinted polymer is applied to a gate electrode. Then, the present inventors have encountered a new technical problem: in a biosensor in which a molecular imprinted polymer is applied to a gate electrode, made by a simple method, certainly, the specificity to a substance to be detected improves compared with conventional art, but due to the thickness of the molecular imprinted polymer layer, the detection sensitivity to the substance to be detected and the stability of detection decrease slightly.

Here, the present inventors have applied a polymer control technique mainly used in the field of polymer chemistry to the present technical field to succeed in controlling the film thickness of the molecular imprinted polymer layer applied to the gate electrode, thereby being able to make the molecular imprinted polymer layer an ultrathin film layer. A gate electrode having an ultrathin film molecular imprinted polymer layer has not only detection specificity to a substance to be detected but also extremely high detection sensitivity (also see the results of Examples in the present application).

Further, surprisingly, in the present invention, by making the molecular imprinted polymer layer applied to the gate electrode an ultrathin film layer, the time from the passage of a current through the apparatus to the stabilization of the potential of the gate electrode surface (that is, the time from when the switch of a measurement apparatus is turned on to when the apparatus reaches a state in which the start of measurement is possible) has been significantly reduced, and the time from the start of measurement to the completion of the measurement has also been significantly reduced (also see the results of Examples in the present application).

In other words, the biosensor of the present invention is an apparatus that has both high detection sensitivity and detection specificity to a substance to be detected and is further also excellent in practicality.

In other words, in one embodiment, the present invention relates to a biosensor comprising: an identification substance capable of binding to a substance to be detected; and an electrode charged with a charge of the identification substance, and detecting a change in a charge density of the electrode caused by binding of the substance to be detected to the identification substance, wherein a polymer layer in which a molecular template having a structure complementary to a molecular structure of the substance to be detected is formed is formed on all or part of a surface of the electrode, the identification substance is contained in the polymer layer, and the polymer layer is an ultrathin film layer.

In one embodiment of the present invention, the ultrathin film layer is a thin film layer having a thickness of 1 μm or less.

In one embodiment of the present invention, the polymer layer is formed by a method comprising (a): a step of polymerizing a monomer solution comprising one or more monomers, the substance to be detected, and the identification substance on all or part of the surface of the electrode to form a polymer layer being an ultrathin film layer on all or part of the surface of the electrode; and (b): a step of removing the substance to be detected from the polymer layer to form the molecular template having a structure complementary to the molecular structure of the substance to be detected in the polymer layer, after the step (a).

In one embodiment of the present invention, polymerization of the monomer solution is living radical polymerization or electrolytic polymerization.

In one embodiment of the present invention, the living radical polymerization is atom transfer radical polymerization (ATRP), reversible addition-fragmentation chain transfer polymerization (RAFT), or nitroxide-mediated polymerization (NMP).

In one embodiment of the present invention, the living radical polymerization is atom transfer radical polymerization (ATRP), and prior to the step (a), a polymerization-initiating molecule is previously bound to all or part of the surface of the electrode.

In one embodiment of the present invention, the step (a) is a step of applying a monomer solution comprising one or more monomers, the substance to be detected, and the identification substance to all or part of the surface of the electrode using spin coating, and polymerizing the applied monomer solution to form a polymer layer which is an ultrathin film layer, on all or part of the surface of the electrode.

In one embodiment of the present invention, the electrode is a gold electrode, a silver electrode, a copper electrode, or a platinum electrode.

In one embodiment of the present invention, the monomer solution comprises at least one monomer selected from the group consisting of an acrylamide derivative, a methacrylamide derivative, an acrylate derivative, a methacrylate derivative, acrylonitrile, 2-vinylpyridine, 4-vinylpyridine, N-vinyl-2-pyrrolidone, and vinyl acetate.

In one embodiment of the present invention, the electrode is electrically connected to a gate insulating film of a field effect transistor.

In one embodiment of the present invention, the electrode is disposed away from the field effect transistor, and the electrode is electrically connected to the gate insulating film via another metal electrode provided on the gate insulating film and wiring.

In one embodiment of the present invention, the electrode is electrically connected to the gate insulating film by being directly placed on the gate insulating film.

In one embodiment of the present invention, the substance to be detected is a substance derived from a living body, a substance in an environment, or a substance in a food.

In one embodiment of the present invention, the substance derived from a living body is a substance derived from a body fluid.

In one embodiment of the present invention, the body fluid is selected from the group consisting of blood, lymph, tissue fluid, coelomic fluid, digestive fluid, sweat, tears, nasal discharge, saliva, urine, semen, vaginal fluid, amniotic fluid, and milk.

Another embodiment of the present invention relates to an electrode used in a biosensor, the biosensor being a biosensor detecting a change in a charge density of the electrode caused by binding of a substance to be detected to an identification substance, the electrode being an electrode charged with a charge of the identification substance capable of binding to the substance to be detected, a polymer layer in which a molecular template having a structure complementary to a molecular structure of the substance to be detected is formed being formed on all or part of a surface of the electrode, the identification substance being contained in the polymer layer, and the polymer layer being an ultrathin film layer.

Another embodiment of the present invention relates to a method for producing an electrode for use in a biosensor, the biosensor being a biosensor detecting a change in a charge density of the electrode caused by binding of a substance to be detected to an identification substance, the electrode being an electrode charged with a charge of the identification substance capable of binding to the substance to be detected, the method comprising:

(a): a step of polymerizing a monomer solution comprising one or more monomers, the substance to be detected, and the identification substance on all or part of a surface of the electrode to form a polymer layer being an ultrathin film layer on all or part of the surface of the electrode; and (b): a step of removing the substance to be detected from the polymer layer to form a molecular template having a structure complementary to a molecular structure of the substance to be detected in the polymer layer, after the step (a).

In one embodiment of the present invention, the living radical polymerization is atom transfer radical polymerization (ATRP), and the method comprises a step of previously binding a polymerization-initiating molecule to all or part of the surface of the electrode prior to the step (a).

In one embodiment of the present invention, the step (a) is a step of applying a monomer solution comprising one or more monomers, the substance to be detected, and the identification substance to all or part of the surface of the electrode using spin coating, and polymerizing the applied monomer solution to form a polymer layer which is an ultrathin film layer, on all or part of the surface of the electrode.

Inventions arbitrarily combining one or more features of the present invention mentioned above are also included in the scope of the present invention.

DESCRIPTION OF EMBODIMENTS

Figure 1:
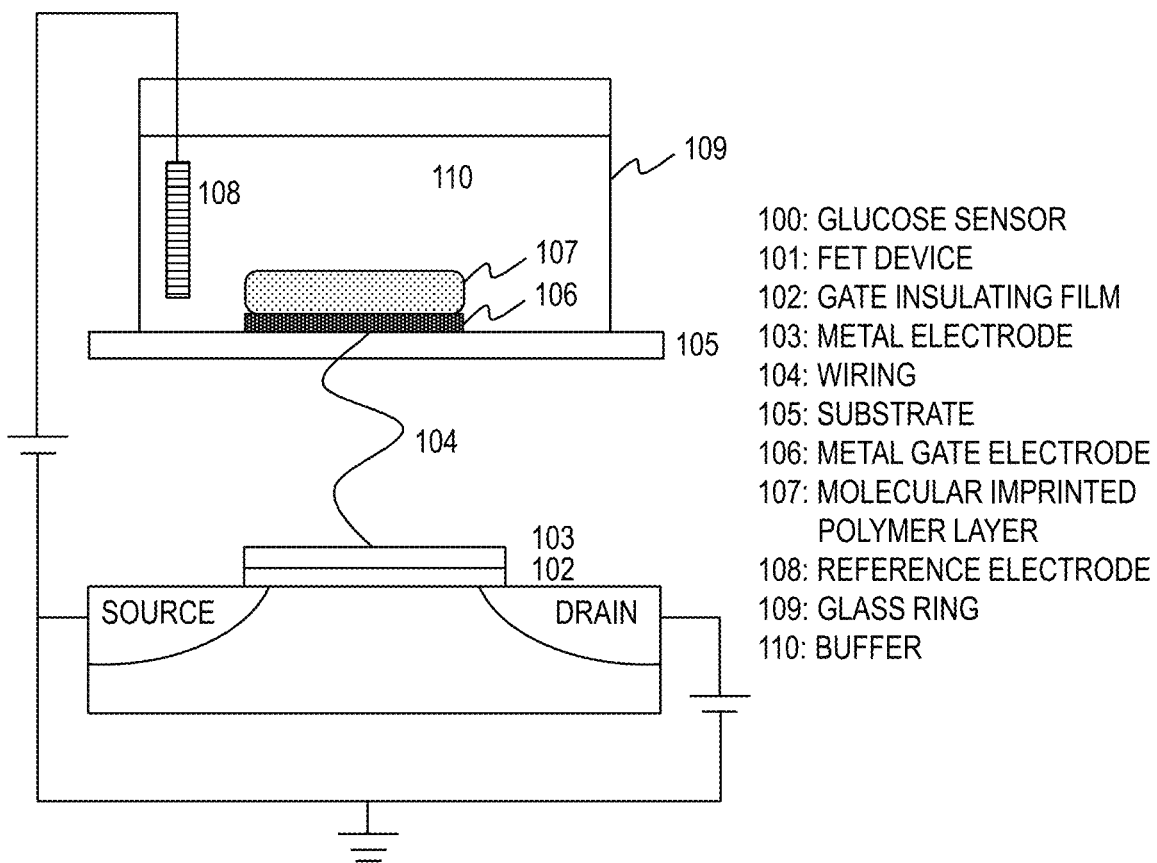
FIG. 1 is a schematic diagram showing the schematic configuration of a glucose sensor that is one embodiment of the present invention.

The biosensor of the present invention is based on the basic principle of detecting, as a change in the charge density of an electrode, an electrical change caused by binding between a substance to be detected and an identification substance capable of specifically or selectively binding to the substance to be detected (the details will be described later). The "substance to be detected" in the present invention is not limited as long as a molecular imprinted polymer corresponding to the substance can be produced. One of ordinary skill in the art can use various substances as objects to be detected based on technical common sense.

The biosensor of the present invention can be used for the detection of a slight amount of a substance in various test samples, and, for example, a substance derived from a living body, a substance in an environment, or a substance in a food can be detected using the biosensor of the present invention. Particularly, in the present invention, even if the concentration of a substance to be detected in a test sample is extremely low, the substance can be detected, and therefore, the present invention can be preferably used for the detection of, for example, a substance in a body fluid (blood, lymph, tissue fluid, coelomic fluid, digestive fluid, sweat, tears, nasal discharge, saliva, urine, semen, vaginal fluid, amniotic fluid, milk, or the like). Examples of the substance in the body fluid include body fluid components (components that are the examination items of general blood biochemical examination, for example, alkaline phosphatase, AST, ALT, lactate dehydrogenase, leucine aminopeptidase, γ-GTP, creatine kinase, cholinesterase, bilirubin, bile acid, albumin, urea nitrogen, creatinine, uric acid, HDL cholesterol, LDL cholesterol, neutral fat, glucose, amylase, lipase, sodium, potassium, chlorine, calcium, inorganic phosphorus, magnesium, zinc, iron, ferritin, C-reactive protein, β2-microglobulin, hemoglobin A1C, glycoalbumin, ammonia, a variety of hormones, and a variety of neurotransmitters (for example, monoamines such as dopamine, adrenaline, noradrenaline, serotonin, melatonin, and histamine; amino acids such as aspartic acid, glutamic acid, γ-aminobutyric acid, glycine, and taurine; acetylcholine; and neuropeptides)), disease-related biomarkers (for example, tumor markers, autoimmune disease markers, central nervous disease markers, and heart disease biomarkers), pathogens (for example, viruses, bacteria, fungi, and parasites) and their related factors, and the drug molecules of previously administered drugs.

The "identification substance capable of binding to a substance to be detected" in the present invention can be appropriately selected by one of ordinary skill in the art according to the substance to be detected, and the identification substance may be a substance capable of specifically binding to the substance to be detected and may be a substance capable of selectively binding to the substance to be detected.

Examples of the "identification substance capable of binding to a substance to be detected" in the present invention can include either one of a pair of substances known to cause specific or selective interaction (for example, glucose and phenylboronic acid, lactic acid and phenylboronic acid, histamine and a carboxyl group monomer, uric acid and a carboxyl group monomer, creatinine and a carboxyl group monomer, sialic acid and phenylboronic acid & an amino group monomer, dopamine and phenylboronic acid & an amino group monomer, or biotin and streptavidin), an aptamer that specifically binds to a particular molecule (for example, a nucleic acid aptamer or a peptide aptamer), either one of a receptor-ligand (or agonist) combination, an antibody that specifically binds to a substance to be detected (for example, a monoclonal antibody that specifically binds to a substance to be detected), or an antigen-binding fragment thereof, and a nucleic acid that specifically binds to a substance to be detected (for example, a nucleic acid having a sequence complementary to that of a target nucleic acid).

In the present invention, the method for forming in a polymer layer a molecular template having a structure complementary to the molecular structure of the substance to be detected is not limited, and various methods known to one of ordinary skill in the art as methods for forming molecular imprinted polymers can be used. Specifically, the molecular imprinted polymer can be made by polymerizing a monomer solution comprising the substance to be detected to form a polymer, and then removing the substance to be detected from the polymer.

In the present invention, the monomer solution for making the molecular imprinted polymer comprises one type or two or more types of monomers. Examples of the monomer contained in the monomer solution include one or more monomers selected from the group consisting of acrylamide derivatives (acrylamide, dimethylacrylamide, N-isopropylacrylamide, N-methylolacrylamide, acryloylmorpholine, and the like), methacrylamide derivatives (methacrylamide, dimethylmethacrylamide, N-isopropylmethacrylamide, N-methylolmethacrylamide, methacryloylmorpholine, and the like), acrylate derivatives (hydroxyethyl acrylate, hydroxypropyl acrylate, dimethylaminoethyl acrylate, dimethylaminopropyl acrylate, and the like), methacrylate derivatives (hydroxyethyl methacrylate, hydroxypropyl methacrylate, dimethylaminoethyl methacrylate, dimethylaminopropyl methacrylate, and the like), acrylonitrile, 2-vinylpyridine, 4-vinylpyridine, N-vinylpyrrolidone, or vinyl acetate.

In the present invention, the method for removing the substance to be detected from the polymer comprising the substance to be detected is not limited and can be appropriately selected by one of ordinary skill in the art according to the type of substance to be detected and the type of monomer used. Non-limiting examples of the substance to be detected-identification substance-removal method combination can include the following:

glucose-phenylboronic acid-hydrochloric acid/methanol lactic acid-phenylboronic acid-hydrochloric acid/methanol histamine-carboxyl group monomer-acetic acid/methanol/acetonitrile uric acid-carboxyl group monomer-acetic acid/methanol/acetonitrile creatinine-carboxyl group monomer-acetic acid/methanol/acetonitrile sialic acid-phenylboronic acid & amino group monomer-hydrochloric acid/methanol dopamine-phenylboronic acid & amino group monomer-hydrochloric acid/methanol The biosensor of the present invention is characterized in that the molecular imprinted polymer layer applied to the electrode surface is an ultrathin film layer. The method for controlling the thickness of the polymer layer is not limited, and various methods known in the field of polymer chemistry can be used. For example, as the method for controlling the thickness of the polymer layer, a method of controlling the thickness of the polymer layer using a chemical method, and a method of making a thin polymer layer using a physical method can be used.

As the method for chemically controlling the thickness of the polymer layer that can be used in the present invention, for example, living radical polymerization and electrolytic polymerization can be used. Particularly, in living radical polymerization, the thickness of the polymer layer can be controlled by polymerization time, and therefore living radical polymerization can be preferably used for the making of a polymer layer having a uniform nano-order thickness.

As living radical polymerization methods, Nitroxide-mediated Polymerization (NMP; for example, Japanese Patent Laid-Open No. 60-89452), Atom Transfer Radical Polymerization (ATRP; for example, National Publication of International Patent Application No. 10-509475), and Reversible Addition-Fragmentation Chain Transfer Polymerization (RAFT; for example, International Publication No. WO 98/01478) are known. In the present invention, a suitable one of any of these polymerization methods can be selected and used according to the properties of the substance to be detected and the required detection procedure.

In addition, an Activator ReGenerated by Electron Transfer (ARGET) ATRP method in which for the purpose of the improvement of the polymerization rate, the simplicity of operation, and the like, a reducing agent is added to reduce divalent copper produced in an ATRP system to continuously active monovalent copper is reported (for example, Angew Chem, Int Ed, 45 (27), 4482 (2006)). In this method, the thickness of the polymer layer can be controlled without requiring an exact vacuum state, and therefore this method can also be preferably used in the present invention.

The polymerization can also be performed without a solvent and can also be performed in a variety of solvents. Examples of preferred solvents can include anisole, toluene, ethylbenzene, tetrahydrofuran, dimethylformamide, and dimethyl sulfoxide.

The amount of the polymerization solvent used is not particularly limited but is preferably within the range of 0 to 2000 parts by mass, more preferably within the range of 10 to 1000 parts by mass, based on 100 parts by mass of the monomer. The upper limit values of these ranges are significant in terms of the suppression of polymerization rate decrease and polymerization control.

For the polymerization-initiating molecule, a compound having a group generally known as a polymerization-initiating molecule for living radical polymerization can be preferably used. For example, alkyl halide organic matter, an organic peroxide, an azo compound, an inorganic peroxide, and a redox type polymerization initiator can be used.

For the polymerization, a catalyst is preferably used. The type of catalyst can be appropriately selected from among a variety of types generally known according to the polymerization method. For example, when ATRP is used as the polymerization method, a metal catalyst comprising a metal such as $Cu(0)$, $Cu^+$, $Cu^{2+}$, $Fe^+$, $Fe^{2+}$, $Fe^{3+}$, $Ru^{2+}$, or $Ru^{3+}$ can be used. In order to achieve a high degree of control of molecular weight and molecular weight distribution, particularly, a monovalent copper compound comprising $Cu^+$, or zerovalent copper is preferred. Specific examples thereof include $Cu(0)$, $CuCl$, $CuBr$, and $Cu_2O$.

In the metal catalyst described above, usually an organic ligand is used. Examples of the coordinating atom to the metal include a nitrogen atom, an oxygen atom, a phosphorus atom, and a sulfur atom. Among them, a nitrogen atom and a phosphorus atom are preferred. Specific examples of the organic ligand include 2,2'-bipyridine and derivatives thereof, 1,10-phenanthroline and derivatives thereof, tetramethylethylenediamine, pentamethyldiethylenetriamine, tris(dimethylaminoethyl)amine (Me6TREN), triphenylphosphine, and tributylphosphine.

Examples of the method for physically controlling the thickness of the polymer layer that can be used in the present invention include a method using spin coating. Specifically, a polymer layer having a nano-order thickness can be made by applying the monomer solution to the target surface, removing the unnecessary monomer solution by high speed rotation using a spin coating apparatus, and then polymerizing the monomer solution. The thickness of the polymer layer made by this method can be adjusted by the rotation speed of the spin coating apparatus.

From the viewpoint of enhancing detection sensitivity, the thickness of the molecular imprinted polymer layer used in the biosensor of the present invention is preferably 1 µm or less. The preferred upper limit and lower limit of the thickness of the molecular imprinted polymer layer used in the biosensor of the present invention differ depending on the substance to be detected, and, for example, the upper limit may be 1 µm, 500 nm, 400 nm, 300 nm, 200 nm, 100 nm, or 50 nm, and the lower limit may be 1 nm, 3 nm, 5 nm, 8 nm, 10 nm, 15 nm, 20 nm, or 30 nm. For example, the thickness of the polymer layer may be 1 nm to 1 µm, preferably 3 nm to 500 nm, further preferably 5 nm to 100 nm, and most preferably 5 nm to 50 nm. As a matter of course, the thickness of the molecular imprinted polymer layer used in the biosensor of the present invention need not be an exactly uniform thickness in its all regions and should be a thickness within the above range on average.

In the present invention, the method for measuring the thickness of the molecular imprinted polymer layer is not particularly limited, and the thickness of the molecular imprinted polymer layer can be measured using any method known in the technical field. For example, the thickness of the molecular imprinted polymer layer can be measured using a commercial ellipsometer or atomic force microscope (AFM).

[Configuration of Biosensor]

One example of a biosensor according to one embodiment of the present invention is shown in FIG. 1, and its configuration will be described. FIG. 1 is a schematic diagram showing the schematic configuration of a glucose sensor 100 that is one embodiment of the present invention. In the following description, a case where the substance to be detected is glucose, and the so-called Extended-gate type FET is used as a detection element will be described as an example, but the biosensor according to the present invention is not limited to such an example. For example, a usual FET in which a gate electrode is directly placed on an insulating film may be used.

In addition, the biosensor according to the present invention is not limited to a biosensor using a FET as a detection element. The essential feature of the present invention is that the presence of the substance to be detected in a test sample is detected as an electrical signal in the electrode portion comprising the ultrathin film molecular imprinted polymer layer, and, for example, the electrode connected to a signal amplifier (for example, a vacuum tube, a transistor, an operational amplifier, or a magnetic amplifier) can also be used as a biosensor.

As shown in FIG. 1, the glucose sensor 100 is a biosensor for detecting a substance to be detected (glucose) using a FET device 101 as a detection element, and mainly comprises a molecular identification member (in FIG. 1, a metal gate electrode 106 and a molecular imprinted polymer layer 107 are collectively referred to as a "molecular identification member") and the detection element 101. The metal electrode 106 is sputtered on a substrate 105, and the molecular imprinted polymer layer 107 is provided on the metal electrode 106. The metal electrode 106 is electrically connected to a metal electrode 103 on an insulating film 102 via wiring 104. The molecular identification member is connected to the FET device via the insulating film 102 and also has a role as the gate electrode in the FET. Here, the molecular imprinted polymer layer 107 comprises phenylboronic acid, and a molecular template having a structure complementary to the molecular structure of glucose is formed on the surface and in the interior of the molecular imprinted polymer layer 107.

A glass ring 109 is fixed on the substrate 105 so as to surround the molecular identification member, and the glass ring 109 is filled with a buffer 110.

As shown in FIG. 1, a reference electrode 108 may be provided as required. The reference electrode 108 is provided in the buffer 110 and forms a closed circuit together with the source electrode and drain electrode of the FET device 101. The reference electrode 108 is an electrode having a reference potential for the measurement of voltage in the FET and may be grounded. Practically, the reference electrode 108 is required in the measurement of voltage in the FET, but the reference electrode 108 need not be provided when it can be replaced by another known method.

The semiconductor substrate of the FET device 101 is, for example, a p-type semiconductor, and the source electrode and the drain electrode are provided in n-type semiconductor portions formed by locally doping parts (for example, two places) of the p-type semiconductor. In other words, the FET used in the glucose sensor 100 is the so-called n-channel type MOSFET (Metal Oxide Semiconductor Field Effect Transistor). The FET used in the biosensor according to the present invention is not limited to the above n-channel type MOSFET (n-MOS) and may be a p-channel type MOSFET (p-MOS), an n-channel junction type FET, or a p-channel junction type FET.

The material of the semiconductor substrate is not particularly limited, and a known semiconductor such as Si, GaAs, a transparent oxide semiconductor (for example, ITO, IGZO, or IZO), an organic semiconductor, or a carbon semiconductor (for example, carbon nanotubes, a graphene semiconductor, or a diamond semiconductor) can be appropriately selected and used. When a carbon semiconductor is used as the material of the semiconductor substrate, the measurement sensitivity of the glucose sensor 100 can be made higher than when Si is used (even if the concentration of the substance to be detected in a test sample is low, measurement can be performed with high precision).

Next, the measurement principle of the glucose sensor 100 according to one embodiment of the present invention shown in FIG. 1 will be described. When a test sample is added to the buffer 110, only glucose molecules in the test sample are incorporated into the molecular template formed on the surface and in the interior of the molecular imprinted polymer layer 107. Since phenylboronic acid that specifically reacts with glucose is contained in the molecular imprinted polymer layer 107, the glucose entering the molecular imprinted polymer layer 107 reacts with the phenylboronic acid. Due to the reaction of the phenylboronic acid in the molecular imprinted polymer layer 107 and the glucose, at least either one of charge density and capacitance in the molecular identification member changes, and the FET detects this as a change in potential, and thus the presence or concentration of the substance to be detected can be measured.

In the glucose sensor 100, as the detection element, an extended-gate type FET is used as described above. In the glucose sensor 100 using the extended-gate type FET, the molecular identification member is separated from the FET body (the FET device 101 comprising the semiconductor substrate in which the source electrode and the drain electrode are provided), and the molecular identification member can be connected removably from the FET device 101.

In other words, the molecular identification member and the FET device can be separately provided and combined. As disclosed in the description of the present application, the molecular identification member can be altered so that various substances to be detected are specifically detected, and therefore, for example, by forming molecular identification members corresponding to various substances to be detected, as chips removable from the detection apparatus body (FET device), diverse factors can be detected by one detection apparatus.

The terms used herein are used to describe particular embodiments, and are not intended to limit the invention, except for particularly defined terms.

The term "comprise" used herein intends that the described item (member, step, factor, number, or the like) is present, and does not exclude other items (members, steps, factors, numbers, or the like) being present, except for cases where the term "comprise" should be clearly differently understood in context.

Unless there are different definitions, all terms (including technical terms and scientific terms) used here have the same meanings as widely understood by one of ordinary skill in the art to which the present invention belongs. The terms used here should be interpreted as having meanings consistent with the meanings herein and in related technical fields and should not be interpreted in an idealized or excessively formal sense unless different definitions are clearly stated.

The present invention will be described below in more detail with reference to Examples. However, the present invention can be embodied in various modes and must not be interpreted as being limited to the Examples described here.

EXAMPLES (Making of Glucose Sensor)

The glucose sensor that was one embodiment of the present invention used in the present Examples was made as described below.

In the present Examples and Comparative Examples, a junction FET (2SK246Y manufactured by TOSHIBA CORPORATION) or a MOSFET (2N7002 manufactured by NXP) was used as a detection element. As the electrode for detecting the charge of the target material, a gold electrode sputtered on a glass substrate was used, and an ultrathin film polymer layer in which a molecular template having a structure complementary to the molecular structure of glucose was formed was made on the gold electrode by a method described later. The above gold electrode was electrically connected to a metal electrode in direct contact with the above junction FET via wiring to form an extended type gate electrode (extended-gate electrode). The above polymer layer comprises in its components a substance that specifically binds to glucose (phenylboronic acid), and when glucose fits in the molecular template formed in the polymer layer, the glucose binds to the phenylboronic acid in the polymer layer. The glucose sensor that is one embodiment of the present invention determines the presence of glucose in the target material by detecting a change in the charge density of the electrode caused by the binding.

In the present Examples, for convenience, the above polymer layer and gate electrode are inclusively referred to as a "molecular identification member".

Next, in the present Examples, in order to perform measurement in a solution, a glass ring having an outer diameter of 20 mm, an inner diameter of 18 mm, and a height of 10 mm, or a glass ring having an outer shape of 12 mm, an inner diameter of 10 mm, and a height of 10 mm was fixed on the molecular identification member obtained as described above, using an epoxy resin.

In the following Examples and Comparative Examples, for glucose sensors comprising ultrathin film molecular imprinted polymer layers made by the method of the present invention, and a glucose sensor comprising a polymer layer made by a conventional method, the speed of the stabilization of the gate surface potential after the start of the passage of a current, detection speed, and detection sensitivity were compared.

Production Example 1: Making of Ultrathin Film Molecular Imprinted Polymer Layer by ATRP Method A glass substrate on which a gold electrode was sputtered was immersed in a 1 mM bis[2-(2-bromoisobutyryloxy)undecyl] disulfide/ethanol solution to bind polymerization-initiating molecules to the gold electrode.

Next, 0.2 g of hydroxyethyl methacrylate (HEMA), 0.1 g of N-3-(dimethylamino)propylmethacrylamide, 0.02 g of vinylphenylboronic acid, 0.02 g of N,N'-methylenebisacrylamide, and 0.009 g of glucose were adjusted to a total amount of 1 g with 6.7% (wt/wt) sodium acrylate (pH 6.8), and then 1 g of dimethylformamide was added for complete dissolution. Then, 100 µl of an aqueous solution of 10 mM copper(II) bromide and 20 mM 2',2' bipyridyl was added, and next, 50 µl of 200 mM ascorbic acid was added.

The glass substrate comprising the gold electrode to which the polymerization-initiating molecules were bound was immersed in this solution for a polymerization reaction under vacuum at 40° C. for 24 hours to make a hydrogel on the gold electrode. After the completion of the polymerization reaction, the gate electrode was immersed in a 0.1 M hydrochloric acid/methanol solution overnight to remove the monomer components and the glucose to make on the gold gate electrode an ultrathin film polymer layer in which a molecular template having a structure complementary to the molecular structure of glucose was formed.

When the thickness of the polymer layer made was visually measured, it was determined as approximately 300 nm.

Comparative Production Example 1: Making of Molecular Imprinted Polymer Layer by Conventional Method 0.2 g of hydroxyethyl methacrylate (HEMA), 0.1 g of N-3-(dimethylamino)propylmethacrylamide, 0.02 g of vinylphenylboronic acid, 0.02 g of N,N'-methylenebisacrylamide, and 0.009 g of glucose were adjusted to a total amount of 1 g and dissolved with 6.7% (wt/wt) sodium acrylate (pH 6.8), and then 10 µl of potassium peroxodisulfate (50 mg/ml, manufactured by Wako Pure Chemical Industries, Ltd.) and 2 µl of tetramethylenediamine (manufactured by TOKYO CHEMICAL INDUSTRY CO., LTD.) as polymerization initiators were added to form a monomer solution.

Next, 10 µl of the monomer solution was added onto a gold gate electrode, an extended type gate electrode, covered with a PET film, and subjected to a polymerization reaction under a nitrogen atmosphere at room temperature for 12 hours to make a hydrogel on the gold electrode. After the completion of the polymerization reaction, the gate electrode was immersed in a 0.1 M hydrochloric acid/methanol solution overnight to remove the monomer components and the glucose to make on the gold gate electrode a polymer layer in which a molecular template having a structure complementary to the molecular structure of glucose was formed.

When the thickness of the polymer layer made was measured, it was approximately 2 µm.

Production Example 2: Making of Ultrathin Film Molecular Imprinted Polymer Layer by ATRP Method A glass substrate on which a gold electrode was sputtered was immersed in a 1 mM bis[2-(2-bromoisobutyryloxy)undecyl] disulfide/ethanol solution to bind polymerization-initiating molecules to the gold electrode.

Next, 0.1 g of N-3-(dimethylamino)propylmethacrylamide, 0.4 g of ethylene glycol dimethacrylate, 0.4 g of vinylphenylboronic acid, and 0.2 g of glucose were adjusted to a total amount of 2 g with ultrapure water, and then 2 g of dimethylformamide was added for dissolution, and nitrogen was passed for degassing. Then, 400 µl of 10 mM copper(II) bromide and 60 mM tris[2-(dimethylamino)ethyl] amine were added, and next, 50 µl of 200 mM ascorbic acid was added.

The glass substrate comprising the gold electrode to which the polymerization-initiating molecules were bound was immersed in this solution for a polymerization reaction under vacuum at 40° C. for 18 hours to make a hydrogel on the gold electrode. After the completion of the polymerization reaction, the gate electrode was immersed in a 0.1 M hydrochloric acid/methanol solution overnight to remove the monomer components and the glucose to make on the gold gate electrode an ultrathin film polymer layer in which a molecular template having a structure complementary to the molecular structure of glucose was formed.

When the thickness of the polymer layer made was visually measured, it was determined as approximately 200 nm.

Production Example 3: Making of Ultrathin Film Molecular Imprinted Polymer Layer by ATRP Method An electrode was immersed in a 1 mM bis[2-(2-bromoisobutyryloxy)undecyl] disulfide/ethanol solution to make polymerization-initiating molecules on the gold substrate. Next, 0.4 g of N-3-(dimethylamino)propylmethacrylamide, 0.04 g of N,N'-methylenebisacrylamide, 0.4 g of vinylphenylboronic acid, and 0.2 g of glucose were adjusted to a total amount of 2 g with ultrapure water, and then 2 g of dimethylformamide was added for dissolution, and nitrogen was passed for degassing. Then, 400 µl of 10 mM copper(II) bromide and 60 mM tris[2-(dimethylamino)ethyl] amine were added, and next, 50 µl of 200 mM ascorbic acid was added. The gold substrate into which the polymerization-initiating molecules were introduced was immersed in this solution for a polymerization reaction under vacuum at 40° C. for 18 hours to make a hydrogel on the gold electrode. After the completion of the polymerization reaction, the gate electrode was immersed in a 0.1 M hydrochloric acid/methanol solution overnight to remove the monomer components and the glucose to make on the gold gate electrode a polymer layer in which a molecular template having a structure complementary to the molecular structure of glucose was formed.

When the thickness of the polymer layer made was visually measured, it was determined as approximately 200 nm.

Biosensors produced by the methods described in Production Examples 1 to 3 and Comparative Production Example 1 all selectively detected glucose (the data are not shown).

(Measurement of Film Thicknesses of Polymer Layers Using Atomic Force Microscope (AFM))

In order to accurately measure the thicknesses of the polymer layers obtained in Production Examples 1, 2, and 3, film thickness measurement using an atomic force microscope (AFM) was performed. Each of the gold substrates provided with the polymer layers obtained in Production Examples 1, 2, and 3 was scratched with a knife, and the height difference between the polymer layer and the gold substrate surface was measured in the air using an atomic force microscope (AFM). The results are shown in FIG. 2.

Figure 2:
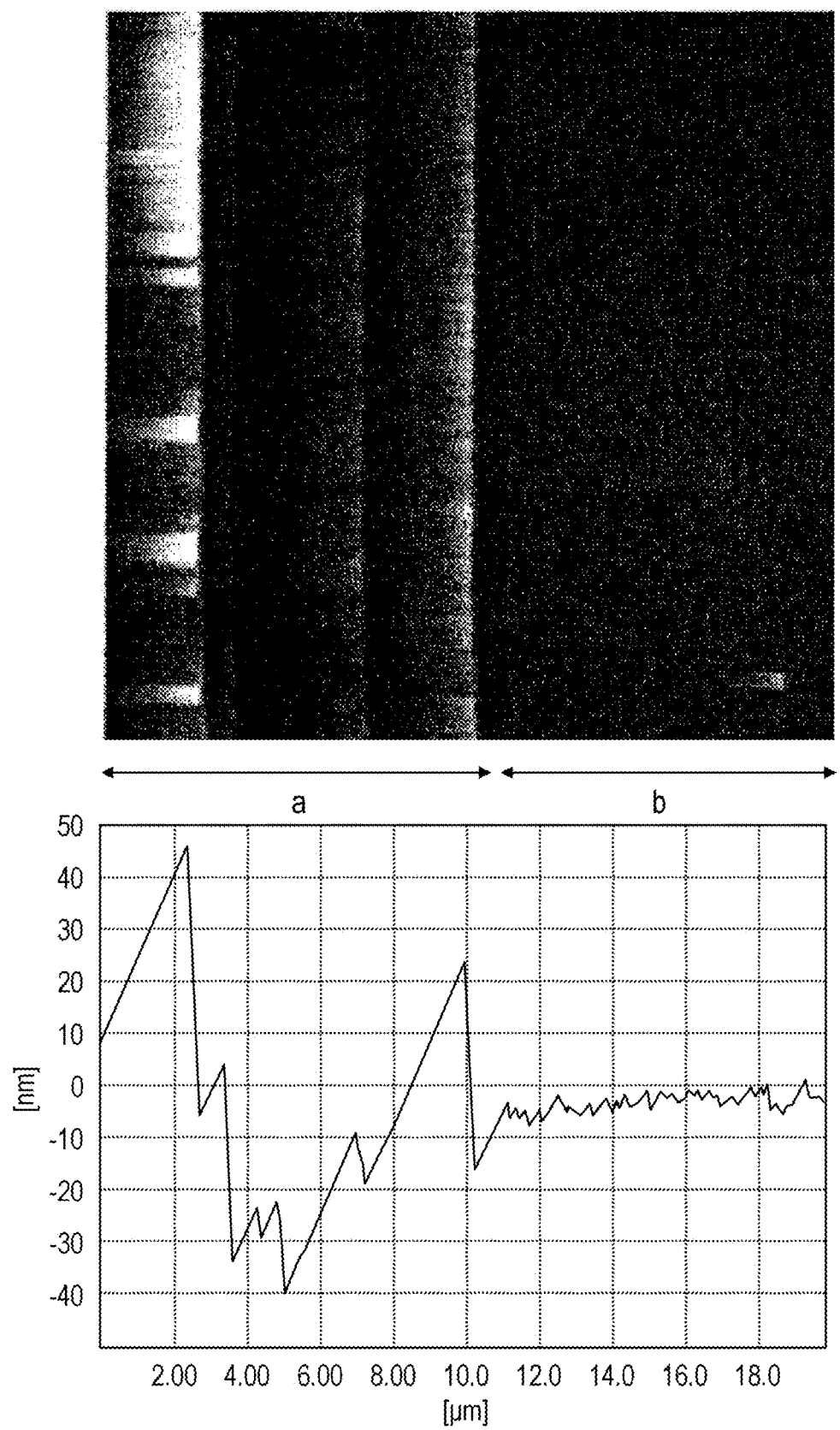
FIG. 2 shows the results of measuring, by an atomic force microscope, the film thickness of a polymer layer made by the method of Production Example 1.
Figure 5:
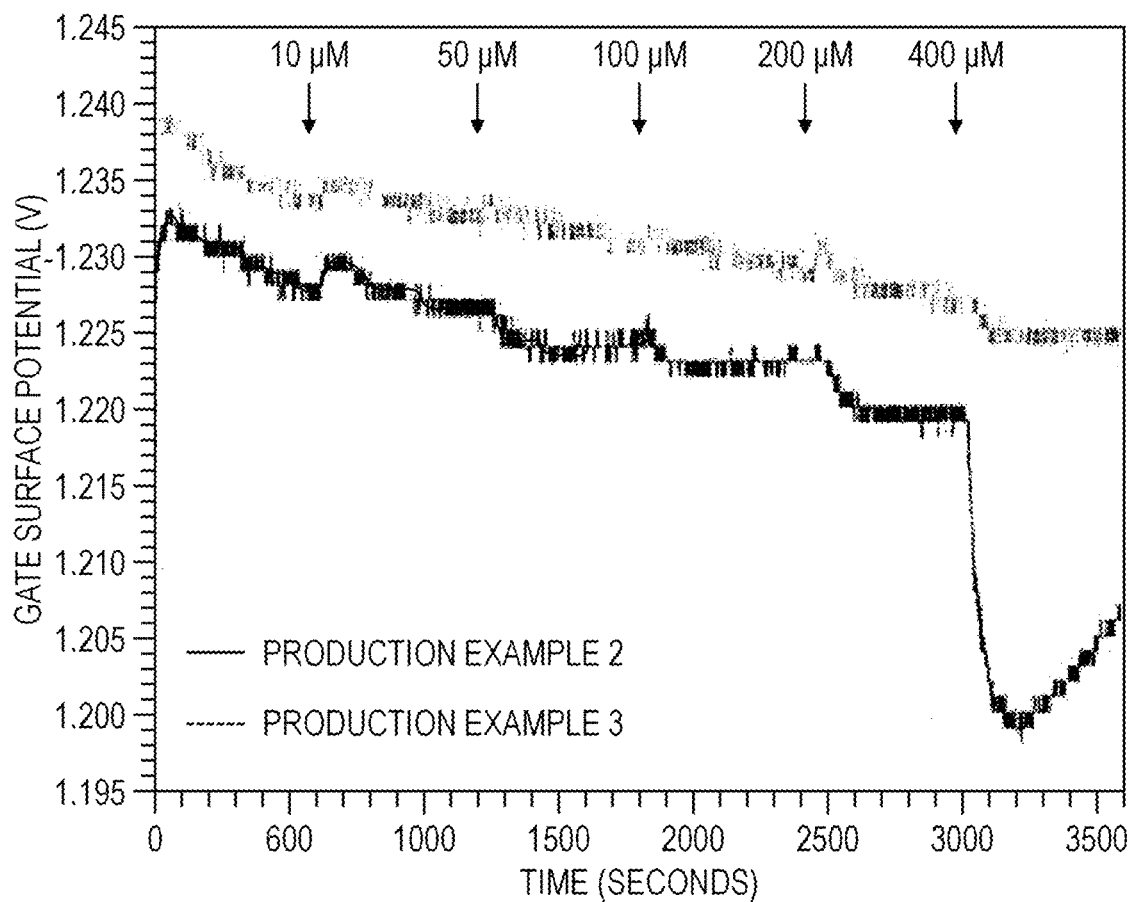
FIG. 5 is a graph comparing the detection of low concentration glucose in the apparatus in Production Example 2 or Production Example 3.

FIG. 2 shows an AFM image and cross-sectional profile of the polymer layer and the gold substrate in Production Example 1. As shown in FIG. 5, the portion shown by (a) is the gold substrate portion exposed by removing the polymer layer, and (b) shows the formed polymer layer. From the cross-sectional profile, the height difference between the polymer layer and the gold substrate was about 30 nm on average. Also for the polymer layers obtained in Production Examples 2 and 3, measurement was performed in the same manner, and as a result, the thicknesses of the polymer layers were about 30 nm on average.

Example 1

In Example 1, experiments were performed using a glucose sensor comprising the ultrathin film molecular imprinted polymer layer made by the method described in Production Example 1, and a glucose sensor comprising the molecular imprinted polymer layer made by the method described in Comparative Production Example 1.

(Evaluation of Time of Stabilization of Gate Surface Potential after Start of Passage of Current)

First, 1500 µl of a 100 mM sodium phosphate buffer (pH 9.0) was added to the gate portion of each of the above glucose sensors, the gold gate electrode and the junction FET were connected, and by a FET real time measurement apparatus (manufactured by Optgenesys Co., Ltd.), a gate voltage of 0 V and a source-drain current of 700 µA were fixed, and the time to the stabilization of the gate surface potential from the start of the passage of a current was measured.

Figure 3:
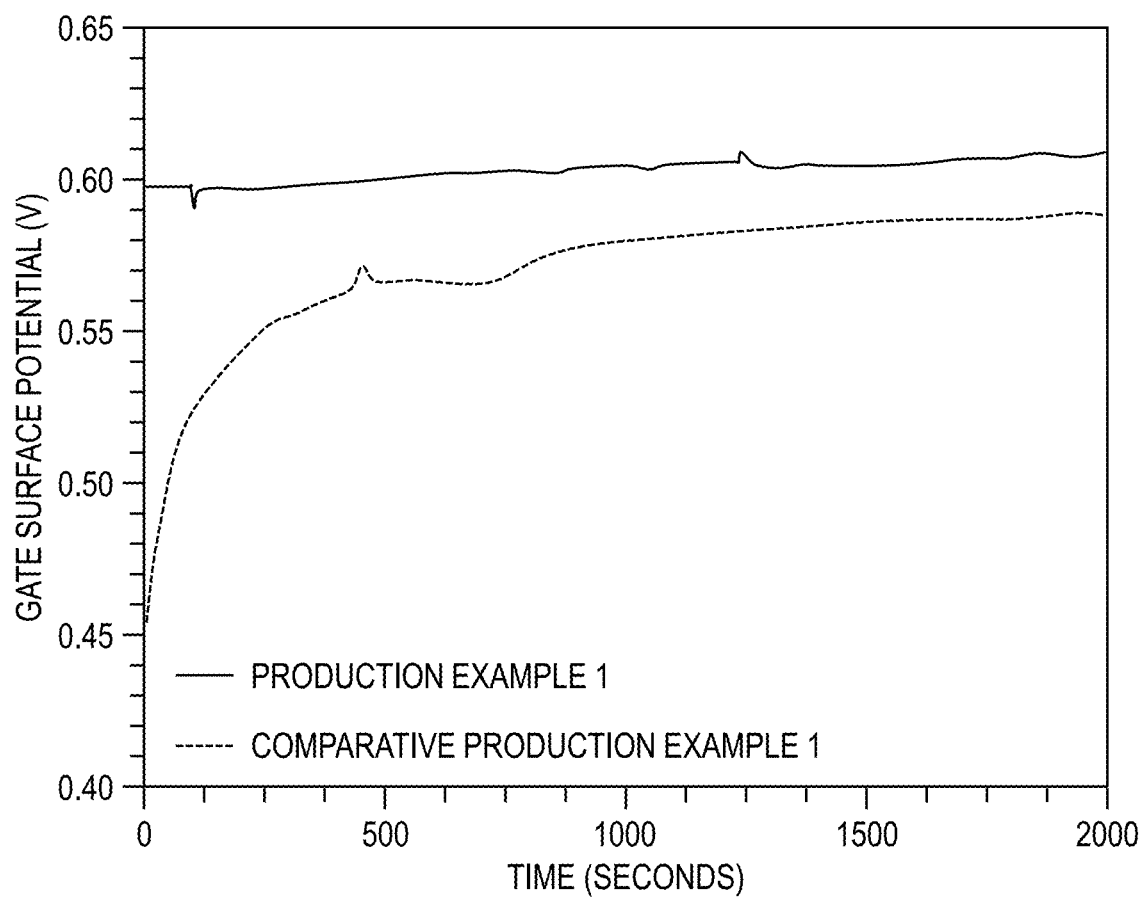
FIG. 3 is a graph comparing the time from the start of the passage of a current to the stabilization of gate surface potential in the apparatus in Production Example 1 or Comparative Production Example 1.

The results of the time to the stabilization of the gate surface potential from the start of the passage of a current are shown in FIG. 3. FIG. 3 is a graph comparing the time from the start of the passage of a current to the stabilization of the gate surface potential in the apparatus in Production Example 1 or Comparative Production Example 1. The vertical axis in FIG. 3 shows a change in the surface potential (V) of the molecular identification member, and the horizontal axis shows measurement time (seconds).

As shown in FIG. 3, it was found that the gate surface potential shown in Example 1 stabilized at a fixed value in several seconds to several tens of seconds. On the other hand, it was found that in the device shown in Comparative Example 1, 1000 seconds to 1500 seconds was required before the gate surface potential stabilized.

In other words, it was shown that in the biosensor of the present invention comprising the ultrathin film molecular imprinted polymer layer, the time from the passage of a current to the stabilization of the gate surface potential (that is, the time from when the switch of the measurement apparatus was turned on to when the apparatus reached a state in which the start of measurement was possible) was extremely short, compared with the biosensor comprising the molecular imprinted polymer layer made by the conventional method, and the biosensor of the present invention was an apparatus excellent in practicality.

(Results of Evaluation of Detection Speed)

Next, in each glucose sensor, 15 µl of a glucose solution at a concentration of 100 mM was added to the sodium phosphate buffer, and a change in gate electrode surface potential was observed.

Figure 4:
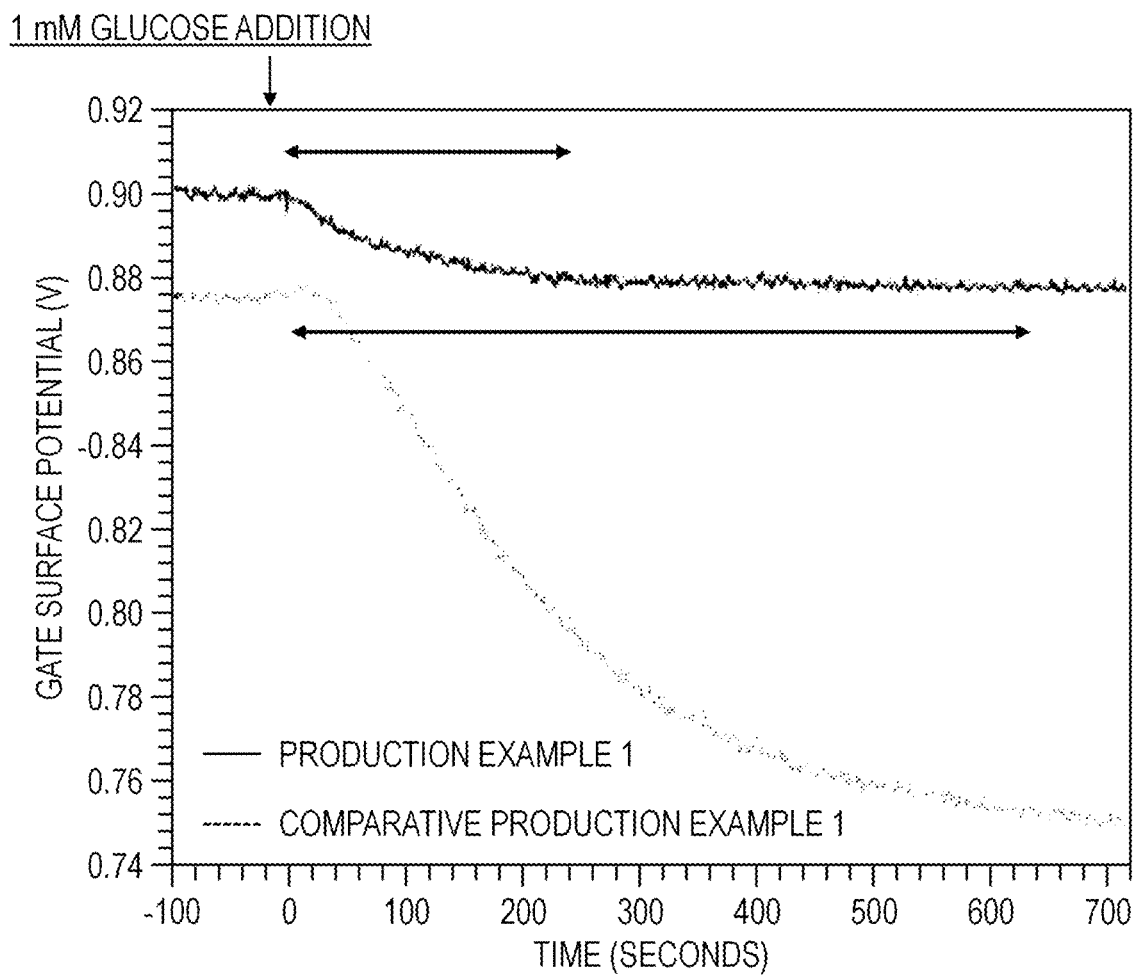
FIG. 4 shows a change in gate surface potential when a glucose solution is added in the apparatus in Production Example 1 or Comparative Production Example 1.

FIG. 4 shows a change in gate surface potential when the glucose solution is added in the apparatus in Production Example 1 or Comparative Production Example 1.

As shown in FIG. 4, in the glucose sensor comprising the ultrathin film molecular imprinted polymer layer made by the method of Production Example 1, the change in gate surface potential was completed by 200 seconds, and then the gate surface potential stabilized. On the other hand, in the glucose sensor comprising the molecular imprinted polymer layer made by the method of Comparative Production Example 1, the gate surface potential continued to change even after a lapse of 600 seconds.

In other words, it was shown that in the biosensor of the present invention comprising the ultrathin film molecular imprinted polymer layer, the time from the start of measurement to the completion of the measurement was extremely short, compared with the biosensor comprising the molecular imprinted polymer layer made by the conventional method, and also in this respect, the biosensor of the present invention was an apparatus excellent in practicality.

Example 2

In Example 2, an experiment was performed using a glucose sensor comprising the ultrathin film molecular imprinted polymer layer made by the method described in Production Example 2, and a glucose sensor comprising the ultrathin film molecular imprinted polymer layer made by the method described in Production Example 3. Production Example 2 and Production Example 3 are different from the molecular imprinted polymer layer in Production Example 1 in the composition of the monomers used for the making of the polymer layer.

(Detection of Low Concentration Glucose)

500 μl of a 100 mM sodium phosphate buffer (pH 9.0) was added to the gate portion of each of the above glucose sensors, the gold gate electrode and the junction FET were connected, and by a FET real time measurement apparatus (manufactured by Optgenesys Co., Ltd.), a gate voltage of 0 V and a source-drain current of 700 μA were fixed, and the glucose sensor was allowed to stand until the gate surface potential stabilized. After the gate surface potential stabilized, a glucose solution at each concentration was added to the sodium phosphate buffer.

The response results when low concentration glucose is added are shown in FIG. 5. As shown in FIG. 5, in the glucose sensors comprising the ultrathin film molecular imprinted polymer layers made by the methods described in Production Example 2 and Production Example 3, a gate surface potential change was observed even at 10 μM, the lowest concentration.

In other words, it was shown that the biosensor of the present invention comprising the ultrathin film molecular imprinted polymer layer had extremely high measurement sensitivity to the material to be measured, compared with the biosensor comprising the molecular imprinted polymer layer made by the conventional method.

It is known that the glucose concentration in each body fluid is about 2.8 mM to 28 mM for blood, about 140 μM to 220 μM for sweat, 6.7 mM or more for urine, and about 50 μM to 500 μM for saliva. In other words, it was shown that by using the present invention, it was possible to detect a slight amount of a substance (for example, glucose) contained in these body fluids.

Production Example 4: Making of Ultrathin Film Molecular Imprinted Polymer Layer by ATRP Method A glass substrate on which a gold electrode was sputtered was immersed in a 1 mM bis[2-(2-bromoisobutyryloxy)undecyl] disulfide/ethanol solution to bind polymerization-initiating molecules to the gold electrode.

Next, 0.2 g of hydroxyethyl methacrylate (HEMA), 0.1 g of N-3-(dimethylamino)propylmethacrylamide, 0.02 g of vinylphenylboronic acid, 0.02 g of N,N'-methylenebisacrylamide, and 0.009 g of glucose were adjusted to a total amount of 1 g with 6.7% (wt/wt) sodium acrylate (pH 6.8), and then 1 g of dimethylformamide was added for complete dissolution. Then, 100 μl of an aqueous solution of 10 mM copper(II) bromide and 20 mM 2',2' bipyridyl was added, and next, 50 μl of 200 mM ascorbic acid was added.

The glass substrate comprising the gold electrode to which the polymerization-initiating molecules were bound was immersed in this solution downward with respect to the solution for a polymerization reaction under vacuum at 40° C. for 6 hours to make a hydrogel on the gold electrode. After the completion of the polymerization reaction, the gate electrode was immersed in a 0.1 M hydrochloric acid/methanol solution overnight to remove the monomer components and the glucose to make on the gold gate electrode an ultrathin film polymer layer in which a molecular template having a structure complementary to the molecular structure of glucose was formed.

When the thickness of the polymer layer made was measured using an ellipsometer, it was approximately 10 nm.

Production Example 5: Making of Ultrathin Film Molecular Imprinted Polymer Layer by ATRP Method A glass substrate on which a gold electrode was sputtered was immersed in a 1 mM bis[2-(2-bromoisobutyryloxy)undecyl] disulfide/ethanol solution to bind polymerization-initiating molecules to the gold electrode.

Next, 0.1 g of N-3-(dimethylamino)propylmethacrylamide, 0.4 g of ethylene glycol dimethacrylate, 0.4 g of vinylphenylboronic acid, and 0.2 g of glucose were adjusted to a total amount of 2 g with ultrapure water, and then 2 g of dimethylformamide was added for dissolution, and nitrogen was passed for degassing. Then, 400 μl of 10 mM copper(II) bromide and 60 mM tris[2-(dimethylamino)ethyl]amine were added, and next, 50 μl of 200 mM ascorbic acid was added.

The glass substrate comprising the gold electrode to which the polymerization-initiating molecules were bound was immersed in this solution for a polymerization reaction under vacuum at 40° C. for 6 hours to make a hydrogel on the gold electrode. After the completion of the polymerization reaction, the gate electrode was immersed in a 0.1 M hydrochloric acid/methanol solution overnight to remove the monomer components and the glucose to make on the gold gate electrode an ultrathin film polymer layer in which a molecular template having a structure complementary to the molecular structure of glucose was formed.

When the thickness of the polymer layer made was measured using an ellipsometer, it was approximately 10 nm.

Example 3

Production Examples 4 and 5 are different from Production Examples 1 to 3 in the monomer composition used for the making of the polymer layer.

The gold substrates comprising the thin film molecular imprinted polymer layers made in Production Examples 4 and 5 were connected to FETs by wiring to form glucose sensors used in Example 3 (other configurations of the sensors were the same as Examples 1 and 2).

First, 500 μl of a 100 mM sodium phosphate buffer (pH 9.0) was added to the gate portion of each of the above glucose sensors, and by a FET real time measurement apparatus, a gate voltage of 0 V and a source-drain current of 90 μA were fixed, and after the gate surface potential from the start of the passage of a current stabilized, a glucose solution at each concentration was added.

Figure 6:
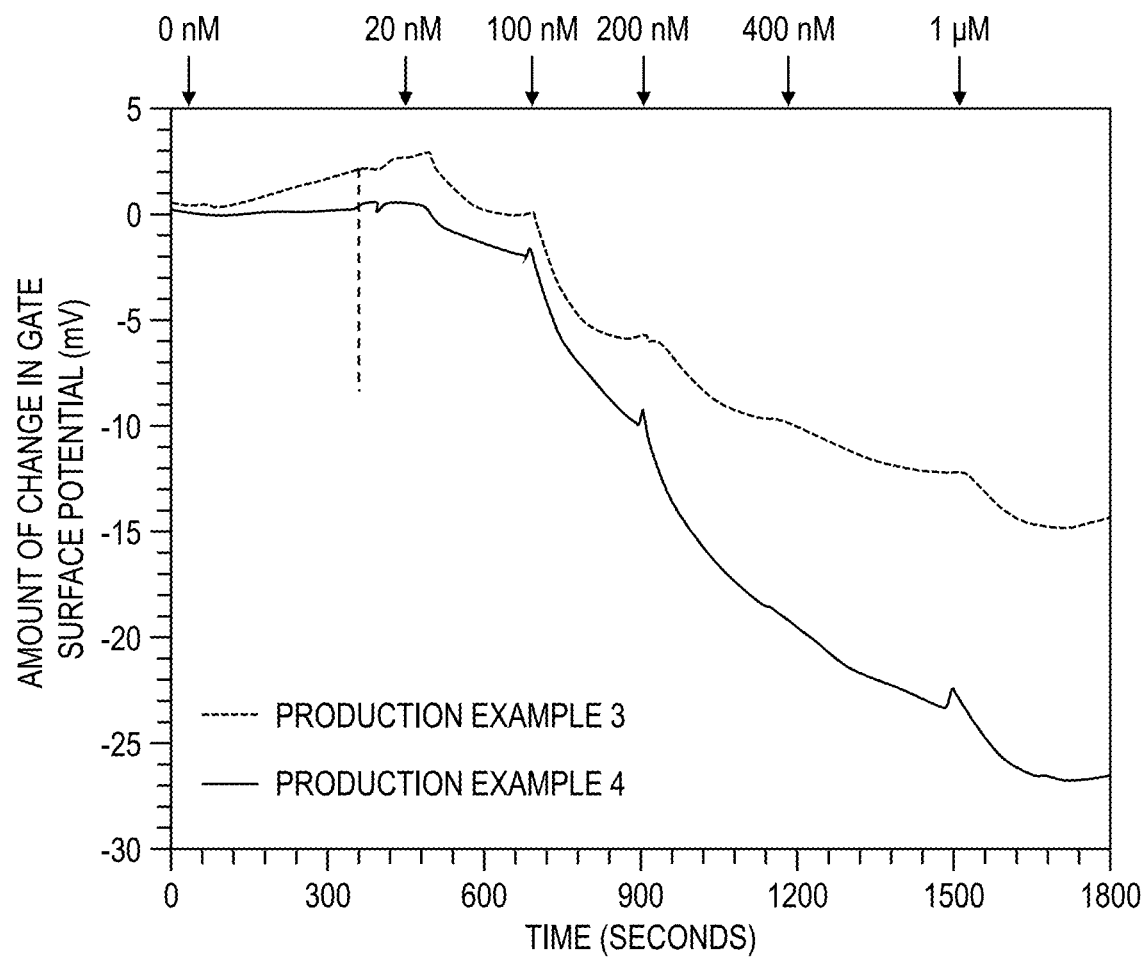
FIG. 6 is a graph comparing the detection of low concentration glucose in the apparatuses in Production Example 4 and Production Example 5.

The results of a change in gate surface potential in the FET when glucose is added at each concentration are shown in FIG. 6. FIG. 6 is a graph plotting the gate surface potential over time in the apparatus in Production Example 4 or 5. The vertical axis in FIG. 6 shows changes in the surface potential (mV) of the molecular identification member, and the horizontal axis shows measurement time (seconds).

As shown in FIG. 6, it was found that the glucose sensors comprising the molecular imprinted polymer layers made in Production Examples 4 and 5 also showed responses to glucose at the extremely low concentration of 20 nM.

Figure 7:
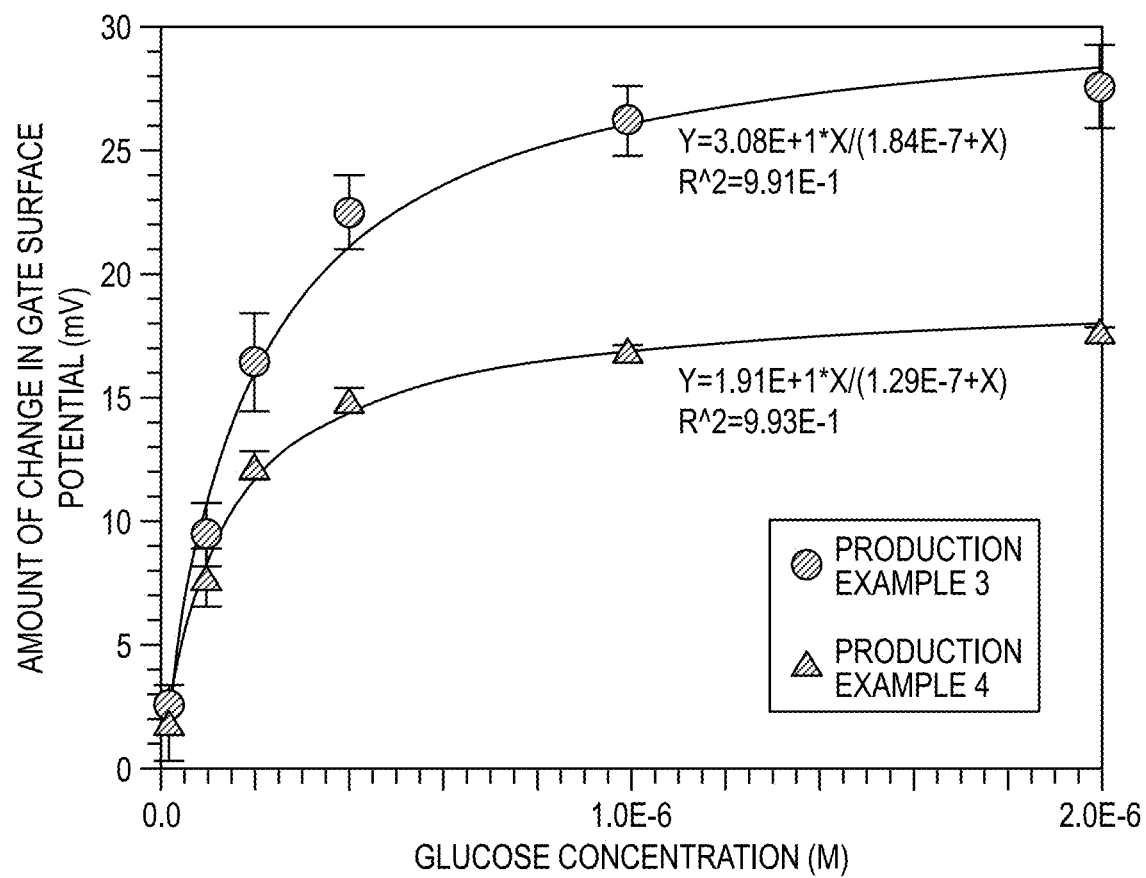
FIG. 7 is a graph showing the amount of change in gate surface potential at the time of the addition of glucose at each concentration in the apparatuses in Production Example 4 and Production Example 5.

FIG. 7 is a graph plotting for each concentration the amount of change in the gate surface potential of the FET responding to glucose at each concentration in FIG. 6, and approximating the plot to Langmuir's adsorption isotherm. As shown in FIG. 7, the measurement results in this experiment were approximated with few variations and errors on the order of nanomoles/liters. In other words, it was found that the glucose sensors of the present invention also had quantitativeness for glucose at extremely low concentration.

In other words, it was shown that the biosensor of the present invention was an apparatus excellent in practicality that had sensitivity sufficient to detect extremely dilute glucose contained in a body fluid such as in tears or saliva, compared with the biosensor comprising the molecular imprinted polymer layer made by the conventional method.

The film thicknesses of the polymer layers obtained in Production Example 4 and Production Example 5 were measured using an ellipsometer (M2000, manufactured by J.A. Woollam Co.). As a result, the film thicknesses when the polymerization-initiating molecules were bound to the gold electrode were 1 to 1.5 nm, and the film thicknesses of the molecular imprinted polymer layers made by the ATRP method were 8 to 25 nm.

Production Example 6: Making of Ultrathin Film Molecular Imprinted Polymer Layer by ATRP Method In the present Production Example, an example in which an ultrathin film molecular imprinted polymer layer using dopamine as a template is made is shown.

A glass substrate on which a gold electrode was sputtered was immersed in a 1 mM bis[2-(2-bromoisobutyryloxy) undecyl] disulfide/ethanol solution to bind polymerization-initiating molecules to the gold electrode.

Next, 0.051 g of N-3-(dimethylamino)propylmethacrylamide, 0.476 g of ethylene glycol dimethacrylate, 0.044 g of vinylphenylboronic acid, and 0.057 g of dopamine were dissolved by adding 1 ml of ultrapure water and 2 ml of dimethylformamide, and nitrogen was passed for degassing. Then, 1.4 mg of copper(II) bromide and 18 mg of tris[2-(dimethylamino)ethyl]amine, and 11 mg of ascorbic acid were added.

The glass substrate comprising the gold electrode to which the polymerization-initiating molecules were bound was immersed in this solution for a polymerization reaction under vacuum at room temperature for 18 hours to make a hydrogel on the gold electrode. After the completion of the polymerization reaction, the gate electrode was immersed in a 0.1 M hydrochloric acid/methanol solution overnight to remove the monomer components and the glucose to make on the gold gate electrode an ultrathin film polymer layer in which a molecular template having a structure complementary to the molecular structure of dopamine was formed.

Example 4

The gold substrate comprising the thin film molecular imprinted polymer layer made in Production Example 6 was connected to a FET by wiring to form a dopamine sensor used in Example 4 (other configurations of the sensor were the same as Examples 1 and 2). As a Comparative Example, a sensor having on a gold gate electrode a polymer layer without a molecular template obtained by excluding dopamine from the monomer solution in the above Production Example was made.

First, 500 μl of phosphate buffered saline (pH 7.4) was added to the gate portion of each of the above dopamine sensors, the gold gate electrode and the MOSFET were connected, and by a FET real time measurement apparatus, a gate voltage of 0 V and a source-drain current of 90 μA were fixed, and after the gate surface potential from the start of the passage of a current stabilized, a dopamine solution at each concentration was added.

Figure 8:
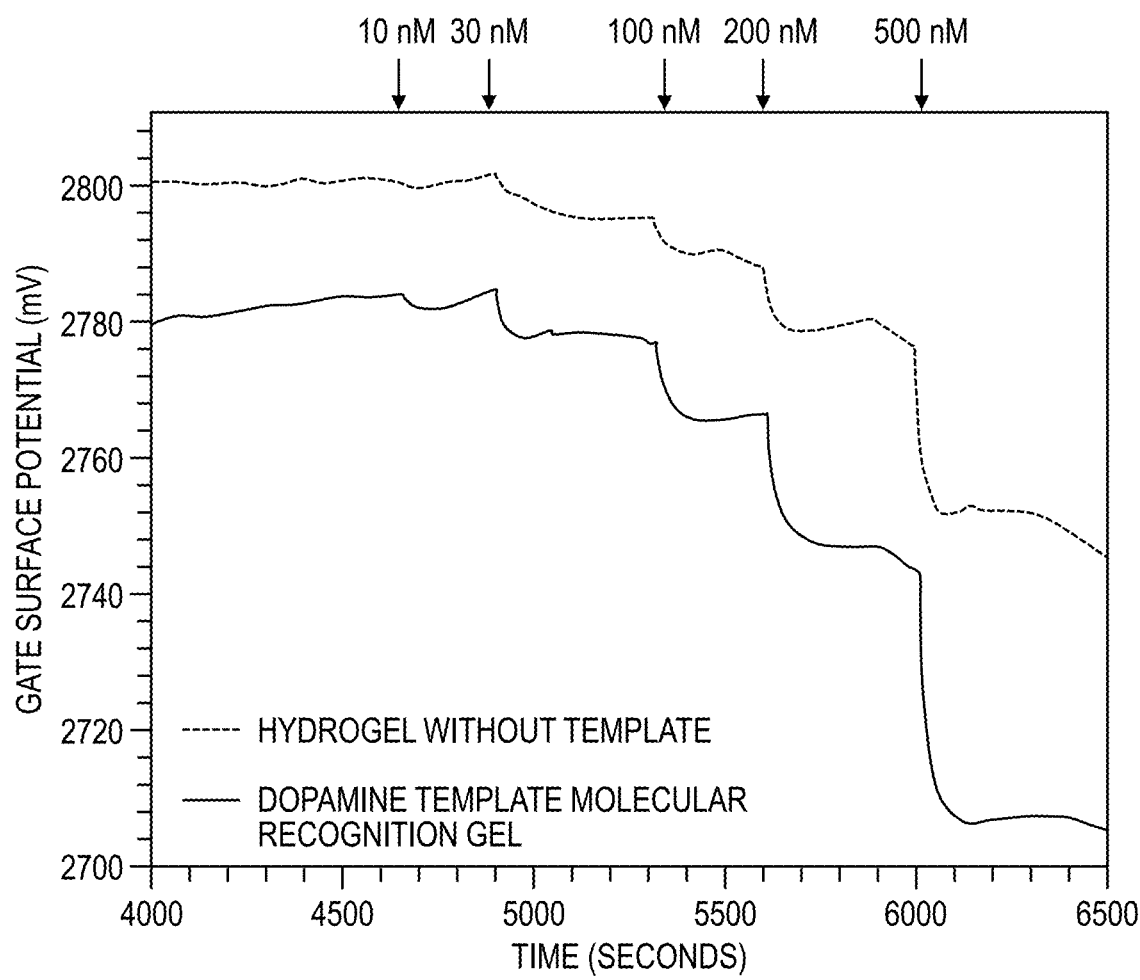
FIG. 8 is a graph comparing the detection of low concentration dopamine in the apparatus in Production Example 6.

The results of a change in gate surface potential in the FET when dopamine is added at each concentration are shown in FIG. 8. FIG. 8 is a graph plotting the gate surface potential over time in the sensor having the molecular imprinted polymer using dopamine as a template that is made in Production Example 6, and the sensor having the polymer layer without a molecular template (Comparative Example). The vertical axis in FIG. 8 shows changes in the surface potential (mV) of the molecular identification member, and the horizontal axis shows measurement time (seconds).

As shown in FIG. 8, it was found that the dopamine sensor comprising the molecular imprinted polymer made in Production Example 6 also showed a response to dopamine at the extremely low concentration of 10 nM.

Figure 9:
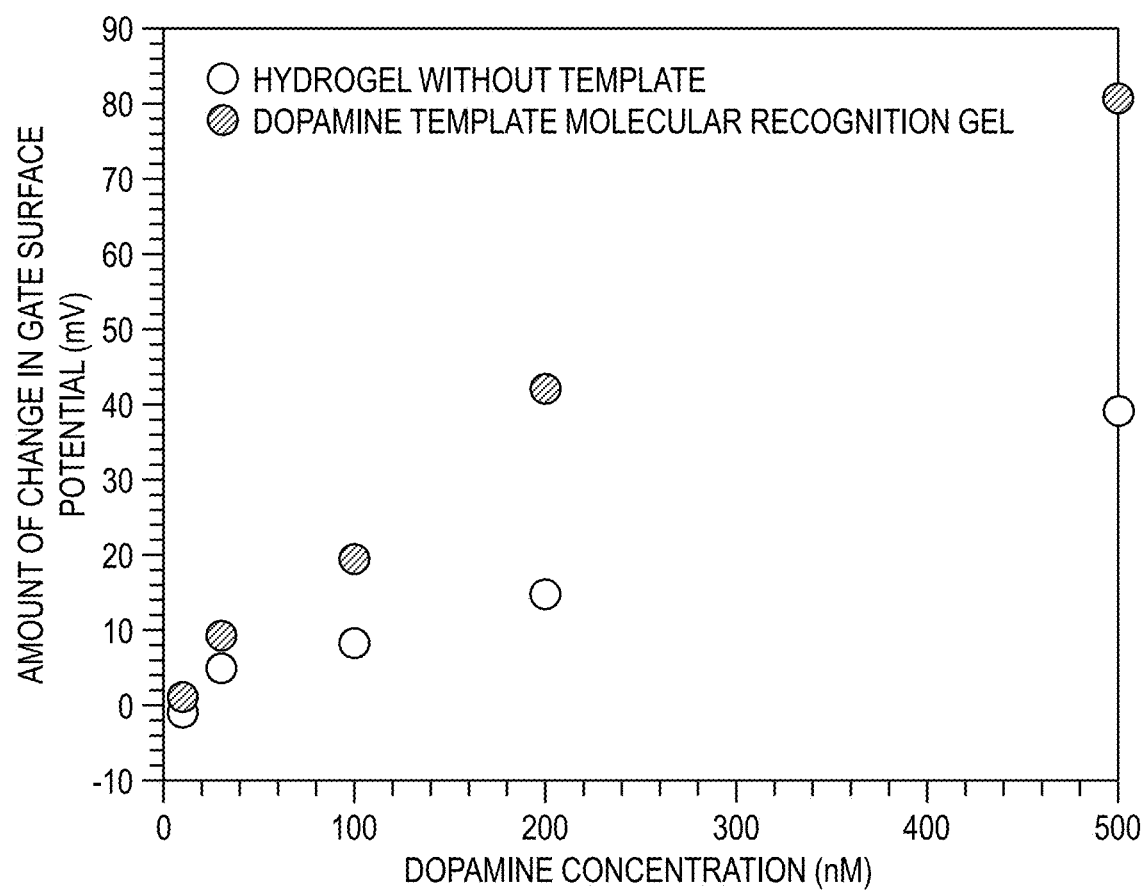
FIG. 9 is a graph showing the amount of change in gate surface potential at the time of the addition of dopamine at each concentration in the apparatus in Production Example 6.

FIG. 9 is a graph plotting for each concentration the amount of change in the gate surface potential of the FET responding to dopamine at each concentration in FIG. 8. As shown in FIG. 9, it became clear that as the concentration of dopamine added increased, a difference occurred between the amount of change in gate surface potential in the sensor comprising the molecular imprinted polymer and the amount of change in gate surface potential in the sensor comprising the gel without a template.

In other words, it was shown that the biosensor of the present invention was an apparatus excellent in practicality that was also able to detect a biomolecule other than glucose selectively and with high sensitivity.

REFERENCE SIGNS LIST

100: glucose sensor
101: FET device
102: gate insulating film
103: metal electrode
104: wiring
105: substrate
106: metal gate electrode
107: molecular imprinted polymer layer
108: reference electrode
109: glass ring
110: buffer

The invention claimed is:
1. A biosensor comprising:
an identification substance capable of binding to a substance to be detected;
an electrode charged with a charge of the identification substance, and able to detect a change in a charge density of the electrode caused by binding of the substance to be detected to the identification substance; and
a polymer layer in which a molecular template having a structure complementary to a molecular structure of the substance to be detected formed on all or part of a surface of the electrode, wherein the identification substance is contained in the polymer layer and the polymer layer is an ultrathin film layer having a thickness of about 5 nm to about 100 nm, wherein the polymer layer is formed by a method comprising:
(a) polymerizing a monomer solution comprising one or more monomers, the substance to be detected, and the identification substance on all or part of the surface of the electrode to form a polymer layer being an ultrathin film layer on all or part of the surface of the electrode, wherein the polymerization of the monomer solution is atom transfer radical polymerization (ATRP); and
(b) removing the substance to be detected from the polymer layer to form the molecular template having a structure complementary to the molecular structure of the substance to be detected in the polymer layer, after (a).

2. The biosensor according to claim 1, wherein prior to (a) a polymerization-initiating molecule is bound to all or part of the surface of the electrode.

3. The biosensor according to claim 1, wherein the electrode is a gold electrode, a silver electrode, a copper electrode, or a platinum electrode.

4. The biosensor according to claim 1, wherein the monomer solution comprises at least one monomer selected from the group consisting of an acrylamide derivative, a methacrylamide derivative, an acrylate derivative, a methacrylate derivative, acrylonitrile, 2-vinylpyridine, 4-vinylpyridine, N-vinyl-2-pyrrolidone, and vinyl acetate.

5. The biosensor according to claim 1, wherein the electrode is electrically connected to a gate insulating film of a field effect transistor.

6. The biosensor according to claim 5, wherein the electrode is disposed away from the field effect transistor, and the electrode is electrically connected to the gate insulating film via another metal electrode provided on the gate insulating film and wiring.

7. The biosensor according to claim 5, wherein the electrode is electrically connected to the gate insulating film by being directly placed on the gate insulating film.

8. The biosensor according to claim 1, wherein the substance to be detected is a substance derived from a living body, a substance in an environment, or a substance in a food.

9. The biosensor according to claim 8, wherein the substance derived from a living body is a substance derived from a body fluid.

10. The biosensor according to claim 9, wherein the body fluid is selected from the group consisting of blood, lymph, tissue fluid, coelomic fluid, digestive fluid, sweat, tears, nasal discharge, saliva, urine, semen, vaginal fluid, amniotic fluid, and milk.

11. An electrode for use in a biosensor, the biosensor being a biosensor for detecting a change in a charge density of the electrode caused by binding of a substance to be detected to an identification substance, the electrode comprising:
a polymer layer in which a molecular template having a structure complementary to a molecular structure of the substance to be detected is formed on all or part of a surface of the electrode, and
an identification substance contained in the polymer layer, wherein the polymer layer is an ultrathin film layer having a thickness of about 5 nm to about 100 nm, and wherein the polymer layer is formed by atom transfer radical polymerization (ATRP),
wherein the electrode is charged with a charge of the identification substance that is capable of binding to the substance to be detected.

* * * * *

UNITED STATES PATENT AND TRADEMARK OFFICE
CERTIFICATE OF CORRECTION

PATENT NO. : 10,996,194 B2  
APPLICATION NO. : 16/087251  
DATED : May 4, 2021  
INVENTOR(S) : Kajisa et al.

It is certified that error appears in the above-identified patent and that said Letters Patent is hereby corrected as shown below:

On the Title Page

(73) Assignees:  
Please correct "THE UNIVERSITE OF TOKYO" to read -- THE UNIVERSITY OF TOKYO --

Signed and Sealed this  
Twenty-fourth Day of August, 2021

Drew Hirshfeld  
*Performing the Functions and Duties of the*  
*Under Secretary of Commerce for Intellectual Property and*  
*Director of the United States Patent and Trademark Office*